United States Patent [19]

Bajard

[11] 4,373,374

[45] Feb. 15, 1983

[54] ARRANGEMENT FOR MEASURING THE AMOUNT OF GAS ENCLOSED IN A LIQUID

[75] Inventor: Jean Bajard, Truchtersheim, France

[73] Assignee: Societe Alsacienne de Services Industriels, Gambsheim, France

[21] Appl. No.: 199,913

[22] Filed: Oct. 23, 1980

[30] Foreign Application Priority Data

Oct. 26, 1979 [FR] France ............................... 79 27108

[51] Int. Cl.³ ............................................... G01N 7/14
[52] U.S. Cl. ...................................................... 73/19
[58] Field of Search ............................................. 73/19

[56] References Cited

U.S. PATENT DOCUMENTS

| 3,077,765 | 2/1963 | Dijkema | 73/19 |
| 3,673,853 | 7/1972 | Griswold et al. | 73/19 |
| 4,120,192 | 10/1978 | Williamson | 73/19 |
| 4,179,918 | 12/1979 | Van Strien | 73/19 |

FOREIGN PATENT DOCUMENTS 2634971 2/1978 Fed. Rep. of Germany ......... 73/19
2036962 7/1980 United Kingdom ..................... 73/19

Primary Examiner—Edward R. Kazenske
Assistant Examiner—Joseph W. Roskos
Attorney, Agent, or Firm—Michael J. Striker

[57] ABSTRACT

An arrangement for automatically measuring the carbonic gas contained in a beverage comprising a measuring chamber communicating with a bypass connected to a main conduit through which the beverage flows, elements in the bypass for alternatingly causing liquid passing through the bypass to flow through the measuring chamber and for preventing communication between the measuring chamber and the bypass so that the liquid will flow directly through the bypass while a sample of the liquid to be analyzed will be enclosed in the chamber, and flexible bellows extending into the measuring chamber for changing the volume of the latter when communication between the measuring chamber and the bypass is interrupted so that a gas pillow will form above the liquid in the measuring chamber the pressure and temperature of which is to be measured to indicate the gas content in the beverage.

8 Claims, 3 Drawing Figures

ARRANGEMENT FOR MEASURING THE AMOUNT OF GAS ENCLOSED IN A LIQUID

BACKGROUND OF THE INVENTION

The present invention relates to an arrangement for automatically measuring the amount of gas enclosed in a liquid, and especially the carbonic gas contained in gaseous beverages such as beer, mineral water, lemonade, fruit juices, etc.

Different apparatus are already known which permit measurement of the amount of gas contained in a liquid, and these apparatus are based on Henry's Law. In accordance with this law, the concentration of the gas dissolved in a liquid is, at each temperature, in direct relation to the pressure of equilibrium created in a volume of gas forming above the liquid. By measuring the pressure and temperature of such a gaseous volume created above a sample of the liquid, it is possible to calculate the concentration of the gas dissolved in the liquid after an equilibrium of the pressure is established.

The French Pat. No. 2,110,826 describes such an arrangement which permits to determine and to automatically interpolate the coordinates of pressure and temperature and to establish by these means the content of a gas in the gaseous liquid. The arrangement shown in the aforementioned French patent has, however, a decisive disadvantage, in that it is necessary for each measurement to eject a portion of the sample to be analyzed to the outside, which creates the danger of bacteriologically contaminating the liquid. Furthermore, sterilization or rinsing is not possible under any conditions, with the arrangement of the prior art.

SUMMARY OF THE INVENTION

It is an object of the present invention to provide an arrangement of the aforementioned kind which avoids the disadvantage of such arrangements known in the art.

It is a further object of the present invention to provide an arrangement which will prevent contamination of the liquid during the measuring of the gas content thereof.

It is a further object of the present invention to provide an arrangement of the aforementioned kind which is composed of relatively few and simple parts so that the arrangement may be manufactured at reasonable cost and stand up perfectly under extended use.

With these and other objects in view, which will become apparent as the description proceeds, the arrangement according to the present invention, for automatically measuring the amount of gas in a liquid, and especially the carbonic gas in gaseous beverages such as beer, mineral water, lemonade, fruit juices, or the like, in which the arrangement is mounted on a loop branching off from a main conduit through which the gas containing liquid passes, and in which the arrangement comprises measuring chamber means destined to enclose a sample of the liquid to be analyzed and communicating with the loop, means in the loop movable between a first position causing the gaseous liquid passing through the loop to flow through the measuring chamber means and a second position preventing communication between the loop and the measuring chamber means so that the liquid will pass directly through the loop while a sample of the liquid to be analyzed will be enclosed in said chamber means, and means for changing the volume of the latter when the communication between the loop and the measuring chamber means is prevented for creating the necessary condition in the measuring chamber means for measuring the amount of gas in the liquid.

The means for changing the volume of the measuring chamber means preferably comprise at least one deformable body extending into the chamber means. Since in the second position of the aforementioned movable means the gas containing liquid will pass directly through the loop, while a sample of the liquid is enclosed in the chamber means, the temperature of the arrangement will be held as stable as possible during the measuring of the gas content in the liquid.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF A PREFERRED EMBODIMENT

Figure 1:
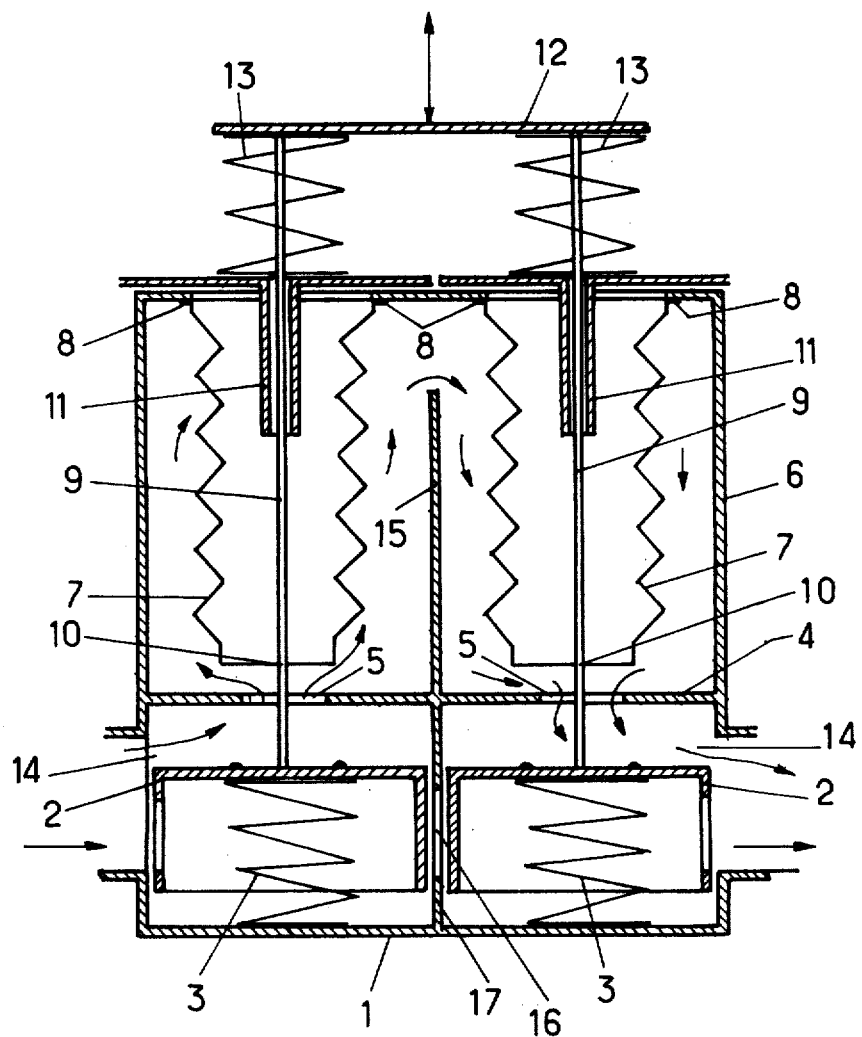
FIG. 1 schematically illustrates the arrangement according to the present invention, in which various elements of the arrangement are shown in a position in which the gas containing liquid passing through the loop is caused to flow through the measuring chamber means.

Referring now to the drawing, and more specifically to FIG. 1 of the same, it will be seen that the arrangement according to the present invention comprises a bypass 1 forming part of the loop connected at opposite ends to a main conduit through which the gas containing liquid flows and two movable closure means in the form of pistons 2 are arranged to be urged by coil springs 3 in upwards direction. The movement of the pistons 2 in upward direction is limited by a separating wall 4 formed with two laterally spaced openings 5 through which the bypass 1 communicates with otherwise closed measuring chamber means 6 mounted above the wall 4. Two deformable bodies 7, shown in the illustrated embodiment as elastic bellows, extend into the measuring chamber means 6, and these bellows are connected at the upper ends at 8 fluid-tightly to the upper wall of the chamber means 6, so as to completely close the latter.

As shown in the drawing, the bellows 7 in the measuring chamber means and the pistons 2 in the bypass are respectively axially aligned and two operating rods 9 extend coaxially through the bellows and with opposite end portions, respectively, upwardly beyond the measuring chamber means 6 and downwardly beyond the separating wall 4. The operating rods 9 are guided for movement in axial direction by tubular guides 11 connected to the top wall of the measuring chamber means 6 and the portions of the rods 9 projecting upwardly beyond the measuring chamber means 6 are connected for simultaneous motion by a traverse 12 and coiled compression springs 13, respectively extending about these upper portions of the rods 9 and abutting with opposite ends respectively against the traverse 12 and the upper wall of the measuring chamber means 6, bias the traverse 12 and the rods 9 fixedly connected thereto in upwards direction. The rods 9 are fixedly and fluid-tightly connected to the closed lower ends of the bellows 7, whereas the portions of the rods 9 projecting downward beyond the closed ends of the bellows extend through the openings 5 in the separating wall 4 and are adapted to engage with their lower ends the pistons 2.

In the circulating position shown in FIG. 1, the traverse 12, which may be moved by any known means against the action of the coil springs 13 in downward direction, is shown in its lowest position in which the operating rods 9 stretch the elastic bellows 7 to a maximum extent, while the lower ends of the rods 9 respectively engage the pistons 2 to move the latter against the coil springs 3 downwardly to a position in which the pistons close an opening 16 formed in a separating wall 17 extending through a partition in the bypass between the two pistons, while at the same time establishing communication between the bypass 1 and the measuring chamber means 6 through the openings 5 in the separating wall 4. This will cause circulation of the liquid through the measuring chamber means 6 which is divided by a partition 15 aligned with the partition 16 into two chambers which communicate with each other and in which the two bellows are respectively arranged. The various arrows indicate the flow of the liquid passing now through the measuring chamber 6, which liquid enters from the bypass 1 through the openings 5 at the left side of the measuring chamber means and passes out of the latter through the opening 5 at the right side thereof.

Figure 2:
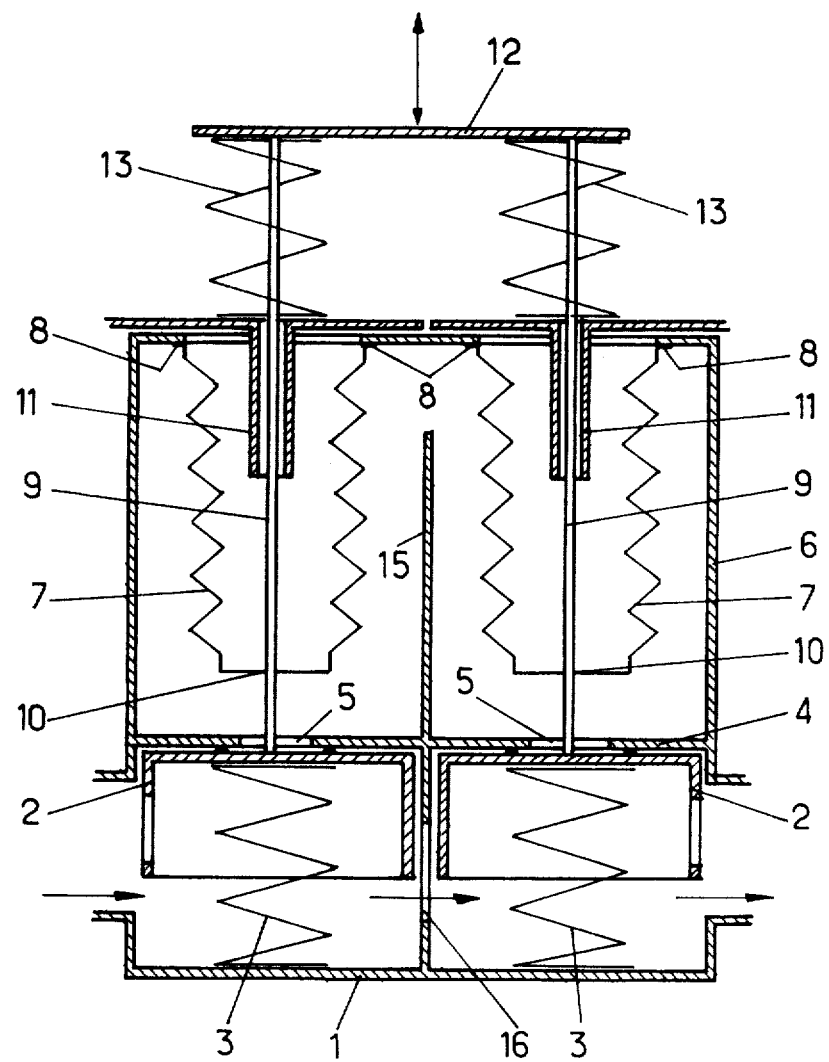
FIG. 2 shows the various elements of the arrangement in a position in which communication between the loop and the measuring chamber means is interrupted, so that a sample of the liquid, the gas content of which is to be measured, is enclosed in the chamber means, while the remaining liquid bypasses the chamber means and flows directly through the loop.

Subsequently thereto, the traverse 12 to which the rods 9 are connected is raised to the position shown in FIG. 2, so that the pistons 2 in the bypass 1 are moved in upward direction by the coil springs 3 cooperating therewith to fluid-tightly close the openings 5 in the separating wall 4, while at the same time opening the opening 16 in the partition 17 so that the fluid will pass directly through the bypass 1 while a sample of the liquid to be tested is enclosed in the measuring chamber means 6.

Figure 3:
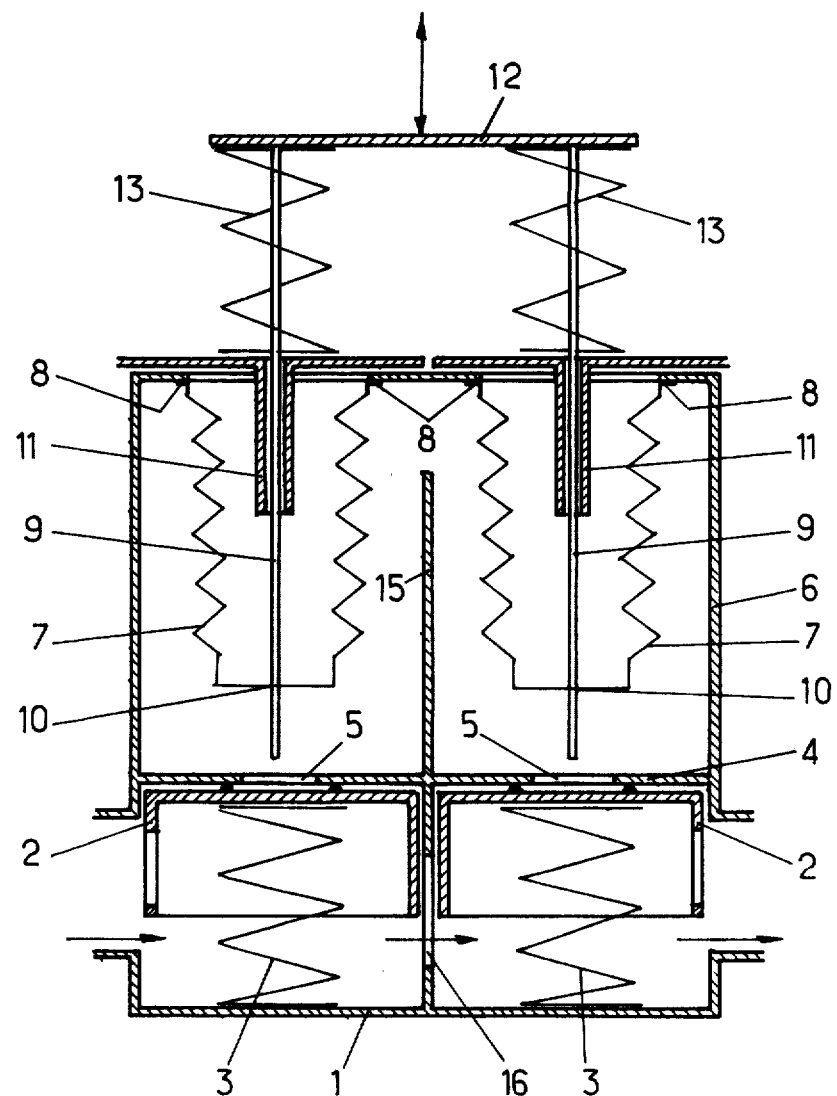
FIG. 3 shows the various elements of the arrangement in a position for measuring the gas content in the liquid.

Finally, in order to measure the content of the gas in the enclosed sample, the traverse 12 is advantageously further moved in upward direction to the position as shown in FIG. 3 so that, by means of the operating rods 9, the elastic bellows 7 are further compressed, and so that, above the liquid enclosed in the measuring chamber 6, a void is formed into which the gas contained in the enclosed liquid sample may escape until a state of pressure equilibrium is formed. At this moment, it is possible, by means generally known, to measure the pressure of the gas formed above the liquid sample enclosed in the measuring chamber 6 as well as the temperature of this gas. The concentration of the gas contained in the liquid may now be calculated from the measured pressure and temperature of the gas in a known manner, preferably by electronic means.

In order to arrive as soon as possible during forming of the gaseous phase at the pressure of equilibrium at which the pressure of the gas is to be measured, it was necessary in the arrangements of the prior art which are based on Henry's Law to incorporate into the arrangement specific means to accelerate the forming of a gas pillow above the enclosed liquid. These means consisted either of electrodes between which an electric tension was established or mechanical means serving to energetically shake the enclosed sample to be analyzed; but in each case these means were distinct of other elements constituting the prior-art arrangements and had the only purpose to accelerate the degassing of the enclosed fluid sample.

The arrangement according to the present invention, however, permits a rapid degassing of the enclosed fluid sample without requiring any additional specific means for this purpose; indeed, it is only necessary for this purpose to carry out the operations described before, and especially to permit a very fast upward movement of the operating rods 9 under the action of the compression springs 13. From this will result, after the closing of the openings 5, a sudden depression of the enclosed sample, and this operation will provoke a shock effect sufficient to produce an instantaneous degassification of the liquid and to rapidly obtain a pressure of equilibrium.

After proceeding in the manner described above, the cycle may be repeated by pushing the traverse 12 downwardly so as to close again the opening 16 in the separating wall 17 while permitting flow of the liquid through the passage 14 and the openings 5 in the separating wall 4 through the measuring chamber 6. In this way, neither the fluid passing through the measuring chamber 6 nor through the bypass 1 is, during the whole operation, in communication with the outer atmosphere, so that any contamination of the fluid is positively prevented.

Another advantage derivable from the arrangement of the present invention is the possibility to reverse the flow of the fluid through the arrangement. As shown in the drawing, the arrangement of the present invention is symmetrical with respect to the right and left parts of the arrangement, which permits to reverse the flow of fluid through the arrangement without modifying the function thereof, after reversing the flow of fluid.

The possibility of reversing the flow of fluid has the following advantage: If the fluid contains impurities or different constituents of solid material (for example, pulp of fruits), it is possible to arrange at the inlet and outlet of the bypass 1 two filters to retain such constituents in order to facilitate proper tight engagement of the pistons 2 with the separating wall 4 during closing of the openings 5, and to realize automatic detachment of the impurities from the filters by periodically reversing the circulation of the fluid. Such inversion of the circulation of the fluids will prevent accumulation of impurities retained at the outer side of the filters.

From the above it will be evident that the arrangement according to the present invention has many advantages as compared with the arrangements up to now known in the art, since with the present arrangement contact of the liquid with the outer atmosphere is positively avoided, and loss of the sample to be measured is prevented, which, if the liquid passing through the arrangement is precious, is of importance. Different operations can follow each other without interruption with a minimum of manual labor. The arrangement of the present invention may be sterilized and rinsed without special precautions together with the conduits connected to the arrangement, through which the liquid flows.

It will be understood that each of the elements described above, or two or more together, may also find a useful application in other types of arrangements for automatically measuring the amount of gas contained in a liquid differing from the types described above.

While the invention has been illustrated and described as embodied in an arrangement for automatically measuring the amount of gas in a liquid, and especially the carbomic gas in gaseous beverages, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An arrangement for automatically measuring the amount of gas in a liquid, and especially the carbonic gas in beverages such as beer, mineral water, sodas, fruit juice, or the like, the arrangement comprising a bypass having an inlet and an outlet and being adapted to be connected into a loop communicating at opposite ends with a main conduit for the liquid; a measuring chamber destined to enclose a sample of the liquid and communicating with said bypass; closure members movable in said bypass between a first position for directing liquid passing through said inlet to flow through said measuring chamber to said outlet while preventing a direct communication between said inlet and said outlet and a second position preventing communication between said bypass and said measuring chamber, so that liquid passing through said inlet will flow directly to said outlet while enclosing a sample of the liquid in said measuring chamber;

a deformable body extending into said measuring chamber for changing the volume of the latter when communication between said measuring chamber and said bypass is prevented for creating in said measuring chamber the necessary condition for measuring the gas content in the liquid; and a single control member operatively connected to said closure members and to said deformable body so that said single control member ensures successively displacement of said movable closure members between said first and second positions and control of said deformable body to modify the volume of the measuring chamber, and vice versa.

2. An arrangement as defined in claim 1, wherein said closure members are pistons.

3. An arrangement as defined in claim 2, wherein said deformable body comprises two elastically extensible and contractable bellows.

4. An arrangement as defined in claim 3, wherein said elastic bellows each extends with a closed end into said measuring chamber and has an opposite end fluid-tightly connected to a wall of the latter.

5. An arrangement as defined in claim 4, further including operating means interconnected between said single control member and said bellows and said pistons and cooperating with said bellows and said pistons for changing the extension of said bellows and for moving said pistons to said first position.

6. An arrangement as defined in claim 5, and including spring means cooperating with said pistons for biasing the latter to said second position, said operating means comprising rods fluid-tightly fixed to said closed ends of respective bellows and each projecting with a portion thereof beyond said closed end and adapted to engage the respective piston to move the latter against the force of said spring means to said first position.

7. An arrangement as defined in claim 1, wherein said measuring chamber is mounted on a wall portion of said bypass and communicates with the latter through two laterally displaced openings in said wall portion, and including a first partition extending between said openings into said measuring chamber short of the wall of the latter opposite said wall portion so as to form at opposite sides of the partition a pair of chambers communicating with each other in the region of said opposite wall, said bypass being provided with a second partition aligned with said first partition and formed with an opening therethrough, said movable closure members being two pistons respectively arranged to opposite sides of said second partition, each movable between a first position closing said opening in said second partition while holding the two laterally displaced openings open and a second position closing said two laterally displaced openings while holding said opening in said second partition open, said deformable body comprising a pair of elastically extensible and contractable bellows respectively arranged in said chambers and respectively axially aligned with said pistons and having each a closed end facing said wall portion and an opposite end fluid-tightly connected to said wall of said measuring chamber opposite said wall portion, and including a pair of axially movable operating rods cooperating with said control member and extending through said bellows fluid-tightly connected to said closed ends of the latter and having opposite ends respectively projecting outside of said measuring chamber and into engagement with the pistons at least when the latter are in said first position, and spring means cooperating with said pistons for biasing the latter to said second position.

8. An arrangement as defined in claim 7, wherein said single control member connects the ends of said operating rods projecting outward of said measuring chamber to each other, and further including spring means cooperating with said control member for biasing the latter away from said opposite wall of said measuring chamber.

* * * * *